(12) United States Patent
Sutermeister et al.

(10) Patent No.: US 7,919,137 B2
(45) Date of Patent: Apr. 5, 2011

(54) MEDICAL DEVICES HAVING ADHERENT POLYMERIC LAYERS WITH DEPTH-DEPENDENT PROPERTIES

(75) Inventors: Derek Sutermeister, Eden Prarie, MN (US); Jay Rassat, Buffalo, MN (US); James Anderson, Fridley, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 79 days.

(21) Appl. No.: 11/983,952

(22) Filed: Nov. 13, 2007

(65) Prior Publication Data

US 2008/0113083 A1    May 15, 2008

Related U.S. Application Data

(60) Provisional application No. 60/858,634, filed on Nov. 13, 2006.

(51) Int. Cl.
*A61L 33/00* (2006.01)
*C08J 7/18* (2006.01)
(52) U.S. Cl. .......................................... 427/2.1; 427/500
(58) Field of Classification Search .................. None
See application file for complete search history.

(56) References Cited

U.S. PATENT DOCUMENTS

| | | | |
|---|---|---|---|
| 5,733,925 A | 3/1998 | Kunz et al. | 514/449 |
| 6,545,097 B2 * | 4/2003 | Pinchuk et al. | 525/240 |
| 2003/0203000 A1 * | 10/2003 | Schwarz et al. | 424/423 |
| 2005/0196518 A1 * | 9/2005 | Stenzel | 427/2.1 |
| 2006/0193890 A1 * | 8/2006 | Owens et al. | 424/423 |
| 2006/0229601 A1 * | 10/2006 | Swoyer et al. | 606/50 |
| 2006/0235503 A1 * | 10/2006 | Llanos et al. | 623/1.13 |

OTHER PUBLICATIONS

L.R. Snyder, "Classification of the Solvent Properties of Common Liquids," *Journal of Chromatographic Science*, vol. 16, Jun. 1978, pp. 223-234.

* cited by examiner

*Primary Examiner* — Shamim Ahmed
(74) *Attorney, Agent, or Firm* — Mayer & Williams PC; David B. Bonham; Keum J. Park

(57) ABSTRACT

According to one aspect of the invention, a method of forming a medical device is provided, which includes: (a) contacting a substrate with a solution that contains (i) one or more types of polymers, (ii) a solvent that contains one or more types of solvent species, and (iii) one or more optional agents, for example, one or more therapeutic agents, among others; and (b) removing the solvent from the solution, thereby forming a polymeric layer on the substrate. The composition of the solution is changed over the course of forming the polymeric layer. In another aspect of the invention, a medical device is provided, which includes a substrate and a polymeric layer over the substrate. The polymeric layer contains a copolymer that contains differing first and second monomers. The lower surface of the polymeric layer contacting the substrate has a surface concentration of the first monomer relative to the second monomer that is higher than that of the upper surface of the polymeric layer opposite the substrate.

21 Claims, 1 Drawing Sheet

MEDICAL DEVICES HAVING ADHERENT POLYMERIC LAYERS WITH DEPTH-DEPENDENT PROPERTIES

STATEMENT OF RELATED APPLICATION

This application claims the benefit of U.S. Provisional Patent Application Ser. No. 60/858,634, filed Nov. 13, 2006, entitled "Medical Devices Having Adherent Polymeric Layers with Depth-Dependent Properties", which is incorporated by reference herein.

FIELD OF THE INVENTION

The present invention relates generally to medical devices, and more particularly to implantable or insertable medical devices which contain adherent polymeric layers.

BACKGROUND OF THE INVENTION

Numerous polymer-based medical devices have been developed for implantation or insertion into the body. For example, various state of the art medical devices consist of a medical device substrate with a polymeric coating that serves as a reservoir for one or more therapeutic agents. Specific examples include drug eluting coronary stents, commercially available from Boston Scientific Corp. (TAXUS), Johnson & Johnson (CYPHER) and others, which have become the standard of care for maintaining vessel patency after balloon angioplasty. These products are based on metallic balloon expandable stents with polymeric coatings that release antiproliferative drugs at a controlled rate and total dose effective to inhibit the smooth muscle proliferation that is associated with restenosis (vessel reclosure).

Various types of polymeric materials have been used as drug-releasing reservoirs, including, for example, homopolymers such as poly(n-butyl methacrylate) and copolymers such as poly(isobutylene-co-styrene), for example, poly(styrene-b-isobutylene-b-styrene) triblock copolymers (SIBS), which are described, for instance, in U.S. Pat. No. 6,545,097 to Pinchuk et al. In addition to their utility as drug delivery reservoirs, SIBS copolymers have proven valuable for a variety of reasons, including their excellent biocompatibility, elasticity, strength, and processability. The latter characteristics are due, at least in part, to the fact that SIBS copolymers are thermoplastic elastomers. Thermoplastic elastomers are elastomeric (i.e., reversibly deformable) polymers that form physical crosslinks which can be reversed, for example, by dissolving or melting the polymer. SIBS triblock copolymers have an elastomeric low glass transition temperature (Tg) midblock and hard elevated Tg endblocks. As with many block copolymers, SIBS tends to phase separate, with the elastomeric blocks aggregating to form elastomeric phase domains and the hard blocks aggregating to form hard phase domains. It has been hypothesized that, because each elastomeric block has a hard block at each end, and because different hard blocks within the same triblock copolymer are capable of occupying two different hard phase domains, the hard phase domains become physically crosslinked to one another via the soft blocks.

SUMMARY OF THE INVENTION

According to an aspect of the invention, a method of forming a medical device is provided, which includes: (a) contacting a substrate with a solution that contains (i) one or more types of polymers, (ii) a solvent that contains one or more types of solvent species, and (iii) one or more optional agents, for example, one or more therapeutic agents, among others; and (b) removing the solvent from the solution, thereby forming a polymeric layer on the substrate. In the method of the present invention, the composition of the solution is changed over the course of forming the polymeric layer.

According to another aspect of the invention, a medical device is provided, which includes a substrate and a polymeric layer over the substrate. The polymeric layer contains a copolymer that in turn contains differing first and second monomers, which may, for example, form first and second polymer blocks, as discussed further below. The lower surface of the polymeric layer contacting the substrate has a surface concentration of the first monomer relative to the second monomer that is higher than that of the upper surface of the polymeric layer opposite the substrate.

These and other aspects and embodiments of the present invention, as well as various advantages, will become immediately apparent to those of ordinary skill in the art upon review of the Detailed Description and Claims to follow.

DETAILED DESCRIPTION OF THE INVENTION

According to an aspect of the invention, a method of forming a medical device is provided, which includes: (a) contacting a substrate with a solution that contains (i) one or more types of polymers, (ii) a solvent that contains one or more types of solvent species, and (iii) one or more optional agents, for example, one or more therapeutic agents, among others; and (b) removing the solvent from the solution, thereby forming a polymeric layer on the substrate. The composition of the solution is changed over the course of forming the polymeric layer, changing the properties of the same.

Preferably, at the beginning of the layer formation process, the composition of the solution is selected to optimize adhesion between the polymeric layer and the substrate, whereas the composition of the solution is subsequently modified in order to provide the layer with another beneficial property, for example, effective drug release characteristics, lower surface tack, and/or an optimized interface, among many others. Generally, the initial solution composition provides greater substrate adhesion than the subsequent solution composition(s).

Figure 1A:
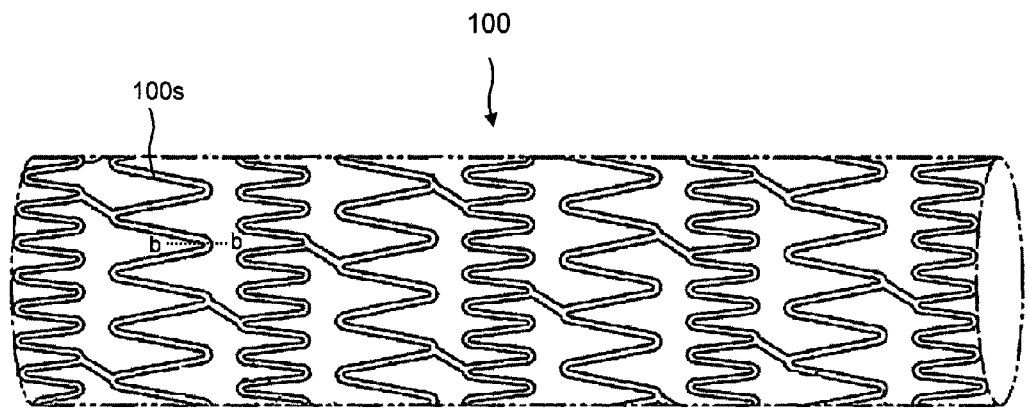
FIG. 1A is a schematic perspective view of a stent in accordance with the prior art.
Figure 1B:
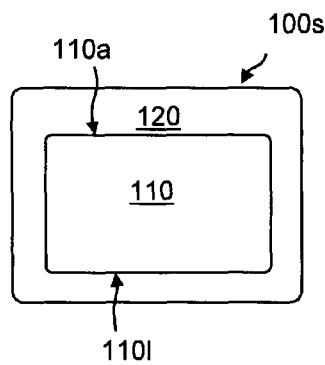
FIG. 1B is a schematic cross-sectional view of the stent of FIG. 1, taken along line b-b.

Such a method may be used, for example, to apply a polymeric layer to a coronary stent substrate, among many other medical device substrates, such as those described below. In this regard, in a current process for forming TAXUS products, the outer surface of a stainless steel coronary stent is sprayed with a solution that contains solvent, paclitaxel and SIBS. Although the solution is spayed on the outside of the stent, the stent is ultimately encapsulated with the polymeric coating due to wicking of the solution around the stent struts. The result of such a process is schematically illustrated, for example, in FIGS. 1A and 1B. FIG. 1A shows a stent 100 which contains a number of interconnected struts 100s. FIG. 1B is a cross-section taken along line b-b of strut 110s of stent 100 of FIG. 1A, and shows a stainless steel stent substrate 110 and a paclitaxel-containing polymeric coating 120, which encapsulates the substrate 110. Typical thicknesses along the exterior (abluminal) surface 110a range from 1 to 50 μm, more typically 15 to 25 μm, whereas typical thicknesses along the interior (luminal) surface 110l also range from 1 to 50 μm, more typically 7 to 15 μm. The solution, which contains paclitaxel, SIBS (16 mol % styrene, 84 mol % isobutylene), and a solvent that consists of 95 vol % toluene and 5 vol % tetrahydrofuran, yields a polymeric layer with a weight ratio of polymer to drug about 10 to 1, and provides a kinetic drug release (KDR) that is safe and effective for the treatment of restenosis. The coating has relatively poor adhesion to the stent substrate surface, but is nonetheless well-secured to the stent substrate as a result of the encapsulation that occurs (and the inherent strength of SIBS).

Figure 2A:
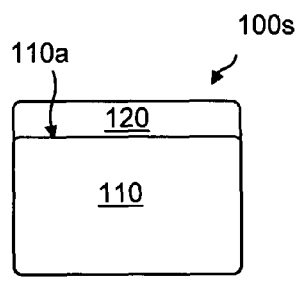
FIG. 2A is a schematic cross-sectional view like that of FIG. 1B, in accordance with an embodiment of the invention.
Figure 2B:
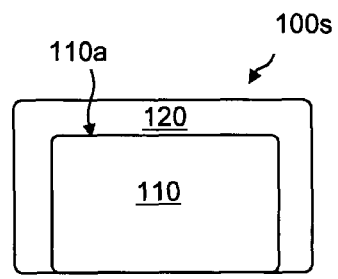
FIG. 2B is a schematic cross-sectional view like that of FIG. 1B, in accordance with another embodiment of the invention.

While it is desirable to provide the abluminal surface of the stent with a polymeric coating that is capable of releasing an antiproliferative drug to combat restenosis, such a drug may not be equally desirable on the luminal surface of the stent and, in fact, may even be detrimental to the extent that it may retard or interfere with the growth of healthy endothelial cells on the luminal surface of the stent. Moreover, the presence of a polymeric layer on the luminal surface is not needed for purposes of promoting biocompatibility, as various stent substrate materials, including stainless steel, are known to support endothelial cell growth. An embodiment of the invention in which a paclitaxel-containing polymeric layer 120 is applied to only the abluminal surface 110a of the stent substrate 110 is illustrated in the strut cross section of FIG. 2A. Another embodiment is illustrated in FIG. 2B, wherein a paclitaxel-containing polymeric layer 120 is applied to the abluminal surface 110a of the stent substrate 110 and on the adjacent edges as well. Such layers 120 may be created, for example, by masking the inner surface of the stent 100 during deposition of the polymer layer, by removing polymeric material from the luminal surface of the stent after creating the polymeric layer 120, by coating a tubular stent precursor with the polymeric layer 120 prior to removing material (e.g., by cutting, punching, etc.) to form the apertures (and thus the struts) of the stent, or by any other suitable methodology.

If such a polymeric layer were to be applied to the stent using the coating solution described above, the polymeric layer could exhibit altered adhesion properties between the stent and the polymeric layer. If the solution composition were to be changed to improve adhesion, the drug release characteristic of the coating, among other properties, could be altered, which may or may not be desirable.

The devices and methods of the present invention address such tradeoffs in properties, among others.

As noted above, methods in accordance with the present invention rely upon a change in solution composition over the course of polymeric layer formation.

For example, at the beginning of the layer formation process, the composition of the solvent may be selected to provide sufficient adhesion of the polymeric layer to the substrate, with the composition of the solvent subsequently being modified in order to provide the layer with another beneficial property, for example, reduced surface tack and/or a drug release profile that has proven to be safe and effective for the treatment of a disease or condition, among others.

As used herein, "treatment" refers to the prevention of a disease or condition, the reduction or elimination of symptoms associated with a disease or condition, or the substantial or complete elimination of a disease or condition. Preferred subjects (also referred to as "patients") are vertebrate subjects, more preferably mammalian subjects and more preferably human subjects.

As used herein a "layer" of a given material is a region of that material whose thickness is small compared to both its length and width. Terms such as "film," "layer" and "coating" may be used interchangeably herein. As used herein a layer need not be planar, for example, taking on the contours of an underlying substrate. Layers can be discontinuous (e.g., patterned).

As used herein a "polymeric layer" is a layer that contains one or more types of polymers, typically containing 50 wt % to 75 wt % to 90 wt % to 95 wt % to 97.5 wt % to 99 wt % polymers, or even more, among other ranges.

Coating thickness may vary widely, for example, ranging from 1 to 2.5 to 5 to 10 to 25 to 50 to 100 μm, with 5 to 30 μm being typical for stent applications among others.

In polymeric layers produced in accordance with the present invention where drug is present, drug may or may not be present throughout the layer. In an example of the latter case, drug may be present throughout the layer, except in the region of the layer that is adjacent to the polymer-substrate interface (e.g., in instances where the drug may interfere with adhesion, etc.).

A wide range of therapeutic agent loadings can be used in conjunction with the polymeric layers of the present invention, with the therapeutically effective concentration and amount being readily determined by those of ordinary skill in the art and ultimately depending, for example, upon the condition to be treated, the age, sex and condition of the subject, the nature of the therapeutic agent, the nature of the polymeric layer, and the nature of the medical device, among other factors. The amount of therapeutic agent commonly ranges from 0.1 to 30 wt %, among other ranges.

As used herein, "polymers" are molecules containing multiple copies (e.g., 5 to 10 to 25 to 50 to 100 to 250 to 500 to 1000 or more copies) of one or more constitutional units, commonly referred to as monomers. Polymers may take on a number of configurations, which may be selected, for example, from cyclic, linear, branched and networked (e.g., crosslinked) configurations. Branched configurations include star-shaped configurations (e.g., configurations in which three or more chains emanate from a single branch point, such as a seed molecule), comb configurations (e.g., configurations having a main chain and a plurality of side chains), dendritic configurations (e.g., arborescent and hyperbranched polymers), and so forth.

As used herein, "homopolymers" are polymers that contain multiple copies of a single constitutional unit. "Copolymers" are polymers that contain multiple copies of at least two dissimilar constitutional units, examples of which include random, statistical, gradient, periodic (e.g., alternating) and block copolymers. As used herein, "block copolymers" are copolymers that contain two or more differing polymer blocks, for instance, because a constitutional unit (i.e., a monomer) is found in one polymer block that is not found in another polymer block. As used herein, a "polymer block" is a grouping of constitutional units (e.g., 5 to 10 to 25 to 50 to 100 to 250 to 500 to 1000 or more units). Blocks can be branched or unbranched. Blocks can contain a single type of constitutional unit ("homopolymeric blocks") or multiple types of constitutional units ("copolymeric blocks") which may be provided, for example, in a random, statistical, gradient, or periodic (e.g., alternating) distribution.

A few examples of block copolymer structures include the following, among others: (a) block copolymers having alternating blocks of the type (AB)m, B(AB)m and A(BA)m where A is a polymer block (e.g., a polystyrene block), B is a different polymer block (e.g., a polyisobutylene block), m is a positive whole number of 1 or more, and (b) block copolymers having multi-arm geometries, such as X(BA)n, and X(AB)n, where n is a positive whole number of 2 or more and X is a hub species (e.g., an initiator molecule residue, a residue of a molecule to which preformed polymer chains are attached, etc.). In addition to the hub species mentioned above, copolymers such as those above can contain a variety of other non-polymer-chain species, which are commonly present in copolymers, including capping molecules, among others. Note that non-polymer species, such as hub species, linking species, etc. are generally ignored in describing block copolymer morphology, for example, with X(BA)2 being designated as an ABA triblock copolymer. Other examples of block copolymers include comb copolymers having a B chain backbone and multiple A side chains, as well as comb copolymers having an A chain backbone and multiple B side chains.

Specific polymers for forming polymeric layers in accordance with the invention may be selected, for example, from suitable members of the following and blends thereof: polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydroxyalkyl celluloses; polyoxymethylene polymers and copolymers; polyimide polymers and copolymers such as polyether block imides and polyether block amides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (cross-linked and otherwise); polymers and copolymers of vinyl monomers including polyvinyl alcohols, polyvinyl halides such as polyvinyl chlorides, ethylene-vinyl acetate copolymers (EVA), polyvinylidene chlorides, polyvinyl ethers such as polyvinyl methyl ethers, polystyrenes, styrene-maleic anhydride copolymers, vinyl-aromatic-olefin copolymers, including styrene-butadiene copolymers, styrene-ethylene-butylene copolymers (e.g., a polystyrene-polyethylenelbutylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene and polystyrene-polyisobutylene-polystyrene block copolymers such as those disclosed in U.S. Pat. No. 6,545,097 to Pinchuk), polyvinyl ketones, polyvinylcarbazoles, and polyvinyl esters such as polyvinyl acetates; polybenzimidazoles; ethylene-methacrylic acid copolymers and ethylene-acrylic acid copolymers, where some of the acid groups can be neutralized with either zinc or sodium ions (commonly known as ionomers); polyalkyl oxide polymers and copolymers including polyethylene oxides (PEO); polyesters including polyethylene terephthalates and aliphatic polyesters such as polymers and copolymers of lactide (which includes lactic acid as well as d-,l- and meso lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of poly(lactic acid) and poly(caprolactone) is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), polyolefin elastomers (e.g., santoprene), ethylene propylene diene monomer (EPDM) rubbers, poly-4-methyl-pen-1-enes, ethylene-alpha-olefin copolymers, ethylene-methyl methacrylate copolymers and ethylene-vinyl acetate copolymers; fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; thermoplastic polyurethanes (TPU); elastomers such as elastomeric polyurethanes and polyurethane copolymers (including block and random copolymers that are polyether based, polyester based, polycarbonate based, aliphatic based, aromatic based and mixtures thereof; examples of commercially available polyurethane copolymers include Bionate®, Carbothane®, Tecoflex®, Tecothane®, Tecophilic®, Tecoplast®, Pellethane®, Chronothane® and Chronoflex®); p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as copolymers of the above.

Particular examples of polymers for coronary stents include SIBS, a blend of SIBS and poly(styrene-co-maleic anhydride) (SMA), poly(lactide-co-glycolide) (PLGA), and poly(N,N'-methylene bisacrylamide) (MBAM), among many others.

Materials for use as underlying substrates include polymeric materials, ceramic materials and metallic materials.

Specific examples of ceramic substrate materials may be selected, for example, from materials containing one or more of the following: metal oxides, including aluminum oxides and transition metal oxides (e.g., oxides of titanium, zirconium, hafnium, tantalum, molybdenum, tungsten, rhenium, and iridium); silicon; silicon-based ceramics, such as those containing silicon nitrides, silicon carbides and silicon oxides (sometimes referred to as glass ceramics); calcium phosphate ceramics (e.g., hydroxyapatite); carbon and carbon-based, ceramic-like materials such as carbon nitrides, among many others.

Specific examples of metallic substrate materials may be selected, for example, from materials containing one or more of the following: metals (e.g., biostable metals such as gold, platinum, palladium, iridium, osmium, rhodium, titanium, tantalum, tungsten, and ruthenium, and bioresorbable metals such as magnesium) and metal alloys, including metal alloys comprising iron and chromium (e.g., stainless steels, including platinum-enriched radiopaque stainless steel), alloys comprising nickel and titanium (e.g., Nitinol), alloys comprising cobalt and chromium, including alloys that comprise cobalt, chromium and iron (e.g., elgiloy alloys), alloys comprising nickel, cobalt and chromium (e.g., MP 35N), alloys comprising cobalt, chromium, tungsten and nickel (e.g., L605), and alloys comprising nickel and chromium (e.g., inconel alloys).

Specific examples of polymeric substrate materials include those that contain one or more suitable polymers selected from those listed above, among others.

Examples of medical devices benefiting from the present invention include implantable or insertable medical devices, for example, catheters (e.g., urological or vascular catheters such as balloon catheters and various central venous catheters), guide wires, balloons, filters (e.g., vena cava filters and mesh filters for distil protection devices), stents (including coronary vascular stents, peripheral vascular stents, cerebral, urethral, ureteral, biliary, tracheal, gastrointestinal and esophageal stents), stent coverings, stent grafts, vascular grafts, abdominal aortic aneurysm (AAA) devices (e.g., AAA stents, AAA grafts), vascular access ports, dialysis ports, embolization devices including cerebral aneurysm filler coils (including Guglilmi detachable coils and metal coils), embolic agents, hermetic sealants, septal defect closure devices, myocardial plugs, patches, pacemakers, lead coatings including coatings for pacemaker leads, defibrillation leads, and coils, ventricular assist devices including left ventricular assist hearts and pumps, total artificial hearts, shunts, valves including heart valves and vascular valves, anastomosis clips and rings, cochlear implants, tissue bulking devices, and tissue engineering scaffolds for cartilage, bone, skin and other in vivo tissue regeneration, sutures, suture anchors, tissue staples and ligating clips at surgical sites, cannulae, metal wire ligatures, urethral slings, hernia "meshes", artificial ligaments, orthopedic prosthesis such as bone grafts, bone plates, joint prostheses, orthopedic fixation devices such as interference screws in the ankle, knee, and hand areas, tacks for ligament attachment and meniscal repair, rods and pins for fracture fixation, screws and plates for craniomaxillofacial repair, dental implants, or other device that is implanted or inserted into the body.

The medical devices of the present invention thus include, for example, implantable and insertable medical devices that are used for systemic treatment, as well as those that are used for the localized treatment of any mammalian tissue or organ. Non-limiting examples are tumors; organs including the heart, coronary and peripheral vascular system (referred to overall as "the vasculature"), the urogenital system, including kidneys, bladder, urethra, ureters, prostate, vagina, uterus and ovaries, eyes, ears, spine, nervous system, lungs, trachea, esophagus, intestines, stomach, brain, liver and pancreas, skeletal muscle, smooth muscle, breast, dermal tissue, cartilage, tooth and bone.

As noted above, the medical devices of the present invention also optionally contain one or more therapeutic agents. "Therapeutic agents," "drugs," "pharmaceutically active agents," "pharmaceutically active materials," and other related terms may be used interchangeably herein. These terms include genetic therapeutic agents, non-genetic therapeutic agents and cells.

Exemplary non-genetic therapeutic agents for use in conjunction with the present invention include: (a) anti-thrombotic agents such as heparin, heparin derivatives, urokinase, streptokinase, alteplase, anistreplase, reteplase, tenecteplase and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) alpha receptor antagonist (such as doxazosin, Tamsulosin) and beta receptor agonists (such as dobutamine, salmeterol), beta receptor antagonist (such as atenolol, metaprolol, butoxamine), angiotensin-II receptor antagonists (such as losartan, valsartan, irbesartan, candesartan and telmisartan), and antispasmodic drugs (such as oxybutynin chloride, flavoxate, tolterodine, hyoscyamine sulfate, diclomine), (u) bARKct inhibitors, (v) phospholamban inhibitors, (w) Serca 2 gene/protein, (x) immune response modifiers including aminoquizolines, for instance, imidazoquinolines such as resiquimod and imiquimod, and (y) human apolioproteins (e.g., AI, AII, AIII, AIV, AV, etc.).

Specific examples of non-genetic therapeutic agents include paclitaxel, (including particulate forms thereof, for instance, protein-bound paclitaxel particles such as albumin-bound paclitaxel nanoparticles, e.g., ABRAXANE), sirolimus, everolimus, tacrolimus, zotarolimus, Epo D, dexamethasone, estradiol, halofuginone, cilostazole, geldanamycin, ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well a derivatives of the forgoing, among others.

Exemplary genetic therapeutic agents for use in conjunction with the present invention include anti-sense DNA and RNA as well as DNA coding for the various proteins (as well as the proteins themselves): (a) anti-sense RNA, (b) tRNA or rRNA to replace defective or deficient endogenous molecules, (c) angiogenic and other factors including growth factors such as acidic and basic fibroblast growth factors, vascular endothelial growth factor, endothelial mitogenic growth factors, epidermal growth factor, transforming growth factor α and β, platelet-derived endothelial growth factor, platelet-derived growth factor, tumor necrosis factor α, hepatocyte growth factor and insulin-like growth factor, (d) cell cycle inhibitors including CD inhibitors, and (e) thymidine kinase ("TK") and other agents useful for interfering with cell proliferation. Also of interest is DNA encoding for the family of bone morphogenic proteins ("BMP's"), including BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Currently preferred BMP's are any of BMP-2, BMP-3, BMP-4, BMP-5, BMP-6 and BMP-7. These dimeric proteins can be provided as homodimers, heterodimers, or combinations thereof, alone or together with other molecules. Alternatively, or in addition, molecules capable of inducing an upstream or downstream effect of a BMP can be provided. Such molecules include any of the "hedgehog" proteins, or the DNA's encoding them.

Vectors for delivery of genetic therapeutic agents include viral vectors such as adenoviruses, gutted adenoviruses, adeno-associated virus, retroviruses, alpha virus (Semliki Forest, Sindbis, etc.), lentiviruses, herpes simplex virus, replication competent viruses (e.g., ONYX-015) and hybrid vectors; and non-viral vectors such as artificial chromosomes and mini-chromosomes, plasmid DNA vectors (e.g., pCOR), cationic polymers (e.g., polyethyleneimine, polyethyleneimine (PEI)), graft copolymers (e.g., polyether-PEI and polyethylene oxide-PEI), neutral polymers PVP, SP 1017 (SUPRATEK), lipids such as cationic lipids, liposomes, lipoplexes, nanoparticles, or microparticles, with and without targeting sequences such as the protein transduction domain (PTD).

Cells for use in conjunction with the present invention include cells of human origin (autologous or allogeneic), including whole bone marrow, bone marrow derived mononuclear cells, progenitor cells (e.g., endothelial progenitor cells), stem cells (e.g., mesenchymal, hematopoietic, neuronal), pluripotent stem cells, fibroblasts, myoblasts, satellite cells, pericytes, cardiomyocytes, skeletal myocytes or macrophage, or from an animal, bacterial or fungal source (xenogeneic), which can be genetically engineered, if desired, to deliver proteins of interest.

Numerous therapeutic agents, not necessarily exclusive of those listed above, have been identified as candidates for vascular treatment regimens, for example, as agents targeting restenosis. Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartan, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, fluvastatin, simvastatin and cerivastatin, (u) fish oils and omega-3-fatty acids, (v) free-radical scavengers/antioxidants such as probucol, vitamins C and E, ebselen, trans-retinoic acid and SOD mimics, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) MMP pathway inhibitors such as marimastat, ilomastat and metastat, (y) cell motility inhibitors such as cytochalasin B, (z) antiproliferative/antineoplastic agents including antimetabolites such as purine analogs (e.g., 6-mercaptopurine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), rapamycin (sirolimus) and its analogs (e.g., everolimus, tacrolimus, zotarolimus, etc.), cerivastatin, flavopiridol and suramin, (aa) matrix deposition/organization pathway inhibitors such as halofuginone or other quinazolinone derivatives and tranilast, (bb) endothelialization facilitators such as VEGF and RGD peptide, and (cc) blood rheology modulators such as pentoxifylline.

Further additional therapeutic agents useful for the practice of the present invention are also disclosed in U.S. Pat. No. 5,733,925 assigned to NeoRx Corporation, the entire disclosure of which is incorporated by reference.

Numerous techniques are available for forming polymeric layers in accordance with the present invention including, for example, solvent spraying techniques, spin coating techniques, web coating techniques, dipping techniques, techniques involving coating via mechanical suspension including air suspension, ink jet techniques, electrostatic techniques, and combinations of these processes, among others.

For example, in some embodiments, a stationary or rotating medical device substrate is spray coated. Coating application rates can vary widely, for example, ranging from 0.1-100 µg/min.

If it is desired to provide one or more therapeutic agents (and/or any other optional agents) within the polymeric layer, so long as these agents are stable under processing conditions, then they may be provided within the solution and co-processed along with the polymer(s). Alternatively, therapeutic and/or other optional agents may be introduced subsequent to the formation of the polymeric layer in some embodiments. For instance, in some embodiments, the therapeutic and/or other optional agents are dissolved or dispersed within a solvent, and the resulting solution contacted (e.g., using one or more of the application techniques described above, such as dipping, spraying, etc.) with a polymer layer.

Several specific embodiments of the invention will now be described with respect to the formation of a polymeric layer based on a copolymer that contains first and second monomers, such as SIBS, SMA or PLG, among many others.

With such copolymers, one of the monomers will commonly be associated with greater adhesion to a given substrate relative to the other. This may be determined, for example, by analyzing homopolymers of each of the monomers. For example, a layer of each of the homopolymers may be formed on the substrate of interest, followed by evaluation of the adhesion of each. Adhesion may be evaluated by tests such as peel tests, friction tests, tack tests, sonication and/or chemical resistance. Examples of ASTM standards include D3330 (15.09)(peel adhesion), D 1894-01 (static and kinetic coefficient of friction for plastic films and sheets), D1623-78, D952-02 (or similar), and A754M-96. In a preferred technique, ASTM D3330 (15.09) is used, with a slight difference in that the adhesion is not of a tape, but rather is of a polymer to a metal interface. Testing may be performed on both dry and wet (after immersion in an aqueous solution) samples, with the latter being employed to give an indication of adhesion behavior in vivo. In this regard, in an initial evaluation step, a fluid may be allowed to soak or flow over the polymer coating for a given amount of time, to qualitatively observe if the adhesion breaks down at the polymer-metal interface.

Assuming that greater adhesion is associated with the second monomer, one can then employ a solvent that has greater affinity for the first monomer relative to the second monomer. Without wishing to be bound by theory, it is believed that in selecting a solvent that has enhanced affinity for the first monomer will concentrate the second monomer (which is associated with greater adhesion) at the interface between the solution and the external environment, which in this instance includes the interface with the substrate. Adhesion is improved as a result.

For example, in SIBS, greater adhesion is associated with the isobutylene (which is rubbery and tacky in homopolymer form) than with the styrene (which is glassy and non-tacky in homopolymer form). By providing a solvent which has greater affinity for the polystyrene blocks, the polyisobutylene blocks are urged to the surface, making the surface tackier and thus providing better adhesion.

One way of selecting a solvent composition that has greater affinity for the first monomer relative to the second monomer is to select a solvent whose polarity more closely matches the polarity of the first monomer than the second monomer. For example, a solvent can be selected whose polarity more closely matches the polarity of a homopolymer of the first monomer than it does the polarity of a homopolymer of the second monomer.

One measure of the polarity of solvents is known as the Snyder Polarity Index (PI). See Snyder, L. J., "Classification of the Solvent Properties of Common Liquids," Chromatography, 92, 1974, 223-230. In the specific case of a paclitaxel-containing SIBS coating, the relevant polarities include those of polystyrene, polyisobutylene, and paclitaxel. Solvent candidates that may selectively uptake each of these entities are as follows: (a) solvents with PI ranging from about 1.8 to 3.0 (candidates for polystyrene uptake), solvents with PI ranging from about 2.9 to 3.7 (candidates for polystyrene uptake), and solvents with PI ranging from about 3.9 to 4.4 (candidates for paclitaxel uptake). Examples of solvents for use with the paclitaxel/SIBS system, as well as various other drug/polymer systems, may be selected from suitable members of those listed in paragraph [0052] of U.S. Pat. App. No. 2003/0203000 to Schwarz, among others. One of ordinary skill in the art can readily experiment with various solvents, including various pure solvents and solvent mixtures, to determine suitable solvent compositions for use in the present invention.

In general, the overall affinity of the solvent for the copolymer is such that the solvent is able to dissolve the copolymer in concentrations sufficient to create a solution suitable for forming a polymeric coating layer. Of course, there are limits to the amount of solute that can be dissolved in any given solvent (i.e., there is a point where precipitates will begin to form in the solution).

Another method for selecting a solvent composition that has greater affinity for one monomer over another is to find a solvent in which the first monomer is more soluble than the second monomer. For example, a solvent can be selected in which a homopolymer of the first monomer has a solubility that is significantly greater (e.g., 2 to 5 to 10 or more times) than that of a homopolymer of the second monomer. Although not a requirement, homopolymers may be of similar molecular weight for the evaluation. Moreover, if a block polymer is being evaluated, solubility may be determined for homopolymers whose molecular weights are similar to those of the polymer blocks within the block copolymer. As above, the overall affinity of the solvent for the copolymer is generally such that the solvent is able to dissolve the copolymer in suitable concentrations.

Again without wishing to be bound by theory, it is believed that selecting a solvent which has enhanced affinity for the first monomer results in higher surface concentrations of the second monomer at the interface with the substrate. In the case of SIBS, by providing a solvent which has greater affinity for polystyrene blocks, the polyisobutylene blocks are urged to the surface, increasing the surface tack and thus providing better adhesion.

Surface concentration may be measured/characterized, for example, by atomic force microscopy (AFM) or X-ray Photoelectron Spectroscopy (XPS), among other techniques.

While the initial solution composition may be selected to provide good adhesion at the substrate interface, the same solution may not provide optimized properties elsewhere within the polymeric layer, including the bulk and/or opposite interface (top surface) of the layer. (For example, in the case of block copolymer, a change in solvent composition will typically result in a change in the way that the phase domains are arranged in the bulk and at the top surface, affecting the properties of these regions.) The solution composition is therefore changed as the layer is deposited to optimize such properties.

Returning again to the example of SIBS, as noted above, adhesion may be improved by choosing a solvent in which uptake of the polystyrene monomer is preferred over the isobutylene, resulting in a higher surface concentration of isobutylene monomer (e.g., in the form of phase domains formed from the polyisobutylene blocks), which leads to greater surface tack. Such surface tack, however, may not be desirable at the outer surface of the stent, because properties associated with the coating surface may lead to issues with the delivery and/or use of the product.

Moreover, in instances where polymeric layers act as drug delivery reservoirs, it has been found that solution composition influences the kinetic drug release (KDR) from the same. Frequently, a solution composition which optimizes adhesion will not be the same as a solution composition for which drug release has been optimized.

In the case of SIBS, and as noted above, a solvent composed of a mixture of toluene and THF is not particularly beneficial from an adhesion standpoint. It may therefore be desirable, for example, to initially apply to the substrate a SIBS solution that contains another solvent composition so as to improve surface adhesion. Once the surface of the substrate is covered with SIBS, the solvent system may be changed, for example, to provide a desired KDR. For example, one could employ a mixture of toluene and THF as a solvent in forming the remainder of the layer, which combination has been demonstrated to release paclitaxel with a KDR that is safe and effective for the treatment of restenosis. In some embodiments, paclitaxel is not included in the initial solution, but is introduced as the solvent is modified.

In some embodiments, the initial solution may be applied until a layer thickness ranging from 0.1 to 0.5 to 1 to 5 µm is established, with the layer continuing to be built up after the solvent change to a thickness ranging from 0.2 to 0.5 to 1 to 5 to 25 to 50 µm.

In some embodiments, there is an abrupt transition in solution composition forming the layer. In others, there is a gradual change in solution composition, leading to a gradient in properties as one proceeds from the lower interface with the substrate to the upper interface.

In addition to the polymer, drug and solvent species that are selected and their relative amounts (which, in addition to affecting various properties of the polymeric layer as previously above, also affect various solution properties, including solution viscosity, surface tension, drying rate, etc.), the coating process is also typically optimized, for example, with respect to substrate surface energy (which affects the wettability of substrate), the coating technique employed (e.g., spray, print, roll, dip, etc), curing/drying conditions, and so forth.

In many of the above embodiments of the invention, the properties of the polymeric layer are optimized by changing the solution concentration. In further embodiments, the properties are optimized by varying the polymer composition of the polymeric solution. For example, an initial solution having a first polymer composition may be applied until a layer thickness ranging from 0.1 to 0.5 to 1 to 5 µm is established, with the layer continuing to be built up after a polymer composition change to a thickness ranging from 0.2 to 0.5 to 1 to 5 to 25 to 50 µm. As above, the composition change may be gradual or abrupt (stepwise).

For example, where a copolymer comprising first and second monomers is employed and where the second monomer provides enhanced adhesion relative to the first monomer, the ratio of the second monomer may be higher in the early stages of layer formation, relative to the latter stages. For instance, in the case of SIBS, the ratio of isobutylene to styrene may be decreased from a mole ratio of, for example, 7 to 10 to 15 to 20 or higher to a molar ratio of 5.25, which has been demonstrated to release paclitaxel with a KDR that is safe and effective for the treatment of restenosis.

As another example, the molecular weight of the coating polymer(s) may be changed as a function of coating depth. For example, the molecular weight(s) of the coating polymer(s) may be changed as one approaches the surface to either increase or decrease surface hardness, among other possibilities.

In embodiments where a blend of polymers is employed within the polymer layer, adhesion may be optimized by varying the ratio of one polymer relative to another within the polymeric solution as a function of coating depth. For example, where a second polymer provides enhanced adhesion relative to a first monomer, the ratio of the second polymer to the first polymer may be higher in the initial stages of layer formation, relative to the latter stages.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A method of forming a medical device comprising: (a) contacting a substrate with a solution that comprises a solvent and a polymer; and (b) removing the solvent from the solution, thereby forming a polymeric layer on the substrate, wherein the composition of the solution is changed from an initial solution composition to a final solution composition over the course of forming the polymeric layer and wherein the initial solution composition which contacts the substrate provides greater adhesion of the polymer to the substrate than does the final solution composition.

2. The method of claim 1, wherein the composition of the solution is changed by changing the solvent composition.

3. The method of claim 2, where the solvent composition is changed by adding a solvent species from the solvent, removing a solvent species from the solvent, or both.

4. The method of claim 2, where the solvent comprises first and second solvent species and the solvent composition is changed by varying the ratio of the solvent species to one another.

5. The method of claim 1, wherein the polymer is a copolymer comprising differing first and second monomers, and wherein a first homopolymer of the first monomer adheres to the substrate better than a second homopolymer of the second monomer.

6. The method of claim 5, wherein the composition of the solution is changed by changing the solvent composition from an initial solvent composition to a final solvent composition.

7. The method of claim 6, wherein the initial solvent composition more closely matches the polarity of the second homopolymer than it does the polarity of the first homopolymer.

8. The method of claim 7, wherein the final solvent composition more closely matches the polarity of the first homopolymer than it does the polarity of the second homopolymer.

9. The method of claim 6, wherein the solubility of the second homopolymer in the initial solvent composition is greater than the solubility of the first homopolymer in the initial solvent composition.

10. The method of claim 9, wherein the solubility of the first homopolymer in the final solvent composition is greater than the solubility of the second homopolymer in the final solvent composition.

11. The method of claim 5, wherein the first monomer is isobutylene and the second monomer is styrene.

12. The method of claim 5, wherein the ratio of the first monomer to the second monomer is greater in the initial solution composition than in the final solution composition.

13. The method of claim 5, wherein the copolymer is a block copolymer comprising a first polymer block of the first monomer and a second polymer block of the second monomer.

14. The method of claim 13, wherein the first monomer is isobutylene and the second monomer is styrene.

15. The method of claim 13, wherein the ratio of the first monomer to the second monomer is greater in the initial solution composition than in the final solution composition.

16. The method of claim 1, wherein the solution comprises differing first and second polymers.

17. The method of claim 16, wherein the composition of the solution is changed by varying the ratio of the polymers to one another.

18. The method of claim 1, wherein the solution comprises a therapeutic agent.

19. The method of claim 18, wherein the therapeutic agent is selected from anti-thrombotic agents, anti-proliferative agents, anti-inflammatory agents, anti-migratory agents, agents affecting extracellular matrix production and organization, antineoplastic agents, anti-mitotic agents, anesthetic agents, anti-coagulants, vascular cell growth promoters, vascular cell growth inhibitors, cholesterol-lowering agents, vasodilating agents, agents that interfere with endogenous vasoactive mechanisms, and combinations thereof.

20. The method of claim 1, wherein the substrate is a metallic substrate.

21. The method of claim 1, wherein the medical device is selected from a stent, a filter, a lead for a cardiac rhythm management (CRM) device, a sensor, a valve and an aneurism filler coil.

* * * * *

UNITED STATES PATENT AND TRADEMARK OFFICE
CERTIFICATE OF CORRECTION

| | | |
|---|---|---|
| PATENT NO. | : 7,919,137 B2 | |
| APPLICATION NO. | : 11/983952 | |
| DATED | : April 5, 2011 | |
| INVENTOR(S) | : Derek Sutermeister, Jay Rassat and James Anderson | |

It is certified that error appears in the above-identified patent and that said Letters Patent is hereby corrected as shown below:

Specification, col. 5, line 47, after "polystyrene-" change "polyethylenebutylene-polystyrene" to --polyethylene/butylene-polystyrene--.

Signed and Sealed this
Twelfth Day of July, 2011

David J. Kappos
*Director of the United States Patent and Trademark Office*